US008933268B2

(12) United States Patent
Tortelli et al.

(10) Patent No.: US 8,933,268 B2
(45) Date of Patent: Jan. 13, 2015

(54) PROCESS FOR THE PREPARATION OF DIFLUROACETIC ACID

(75) Inventors: Vito Tortelli, Milan (IT); Cristiano Monzani, Trezzo sull'Adda (IT); Ivan Wlassics, Garessio (IT)

(73) Assignee: Solvay Specialty Polymers Italy S.p.A., Bollate (MI) (IT)

(*) Notice: Subject to any disclaimer, the term of this patent is extended or adjusted under 35 U.S.C. 154(b) by 85 days.

(21) Appl. No.: 13/883,182

(22) PCT Filed: Oct. 28, 2011

(86) PCT No.: PCT/EP2011/068946
§ 371 (c)(1),
(2), (4) Date: May 2, 2013

(87) PCT Pub. No.: WO2012/062602
PCT Pub. Date: May 18, 2012

(65) Prior Publication Data
US 2013/0231502 A1 Sep. 5, 2013

(30) Foreign Application Priority Data
Nov. 8, 2010 (EP) .................................. 10190298

(51) Int. Cl.
C07C 51/41 (2006.01)
C07C 51/02 (2006.01)
C07C 51/00 (2006.01)

(52) U.S. Cl.
CPC .............. *C07C 51/41* (2013.01); *C07C 51/00* (2013.01); *C07C 51/412* (2013.01); *C07C 51/02* (2013.01)
USPC .......................................... 562/541; 562/605

(58) Field of Classification Search
CPC ................. C07C 51/41; C07C 51/02

USPC .................................................... 562/605, 541
See application file for complete search history.

(56) References Cited

U.S. PATENT DOCUMENTS 2,403,207 A * 7/1946 Barrick ........................ 562/113
2,442,995 A 6/1948 Coffman

FOREIGN PATENT DOCUMENTS

| JP | 06-228043 A | 8/1994 |
| JP | 07-242587 A | 9/1995 |
| JP | 2008-162902 A | 7/2008 |
| JP | 2008-280304 A | 11/2008 |
| JP | 2008-280305 A | 11/2008 |

OTHER PUBLICATIONS

Coffman, D. D., et al—"Addition Reactions of Tetrafluoroethylene", 1949, Journal of Organic Chemistry, vol. 14, Issue No. 5, pp. 747-753; 7 pgs.
Raksha, M. A., et al—, "Reaction of tetrafluoroethylene with piperidine. A new method of preparation of difluoroacetic acid", 1964, Zhurnal Obshchei Khimii, vol. 34, Issue No. 10, pp. 3465-3467; Translation provided in English from Zhurnal Obshchei Khimii; includes abstract; 3 pgs.
Oharu, Kazuya, et al—"Synthesis of difluoroacetic acid derivatives via difluoroacetyl fluoride prepared by the gas-phase catalytic decomposition of 1,1,2,2-tetrafluoroethyl alkyl ethers over Al2O3 or ZrO2", 1998, Asahi Garasu Kenkyu Hokoku, Reports Res. Lab. Asahi Glass Co. Ltd., Volume date 1997, Issue No. 47, pp. 69-79; 12 pgs; Includes abstract.

* cited by examiner

*Primary Examiner* — Yevegeny Valenrod
(74) *Attorney, Agent, or Firm* — Xuping Fu

(57) ABSTRACT

A process is provided for the preparation of difluoroacetic acid from tetrafluoroethylene. The process comprises reacting tetrafluoroethylene with an aqueous solution of an inorganic base, optionally in the presence of an organic solvent.

11 Claims, No Drawings

PROCESS FOR THE PREPARATION OF DIFLUROACETIC ACID

CROSS-REFERENCE TO RELATED APPLICATIONS

This application is a U.S. national stage entry under 35 U.S.C. 371 of International Application No. PCT/EP2011/068946 filed Oct. 28, 2011, which claims priority to European application No. 10190298.9 filed on Nov. 8, 2010, the whole content of this application being incorporated herein by reference for all purposes.

TECHNICAL FIELD

The invention relates to a novel process for the preparation of difluoroacetic acid.

BACKGROUND ART

Difluoroacetic acid is used as an intermediate in the pharmaceutical and agrochemical industry. Different ways of preparing difluoroacetic acid or its salts have been disclosed.

For instance it is known to prepare difluoroacetic acid by chlorine-fluorine exchange. JP 06-228043 (ASAHI GLASS CO LTD) 16 Aug. 1994 discloses a reaction of dichloroacetyl chloride with a secondary amine followed by treatment of the N,N-disubstituted dichloroacetamide product with a fluorinating agent, e.g. KF, to give N,N-disubstituted difluoroacetamide. The amide product is hydrolyzed to give difluoroacetic acid.

Preparation of difluoroacetic acid from tetrafluoroethylene has been reported for instance in U.S. Pat. No. 2,442,995 (DU PONT DE NEMOURS & CO.) Aug. 6, 1948 which discloses a process whereby tetrafluoroethylene is reacted with ammonia to yield 2,4,6-tris(difluoromethyl)-s-triazine which is then hydrolyzed in the presence of NaOH to yield difluoroacetic acid.

JP 07-242587 (ASAHI GLASS CO LTD) 19 Sep. 1994 discloses the preparation of difluoroacetic acid by a two-step process wherein tetrafluoroethylene is reacted with a primary or secondary amine in the presence of water and, optionally, a tertiary amine to obtain a difluoroacetamide of formula $CHF_2CONR_1R_2$ which is then hydrolyzed to difluoroacetic acid in the presence of concentrated acids or alkalis.

JP 2008-162902 (CENTRAL GLASS CO LTD) 17 Jul. 2008 discloses the preparation of a difluoroacetic acid metal salt by reaction of a 1-alkoxy 1,1,2,2-tetrafluoroethane ($R^1O-CF_2CF_2H$), e.g. 1-methoxy-1,1,2,2-tetrafluoroethane, with a metal hydroxyde or a metal alkoxide; the 1-alkoxy 1,1,2,2-tetrafluoroethane $R^1O-CF_2CF_2H$ having been prepared by reaction of tetrafluoroethylene with the corresponding alcohol $R^1OH$ in the presence of a base.

These processes have the drawback that complex intermediates (e.g. triazine, amides, alkoxyethanes) have to be prepared and isolated before hydrolysis can be carried out. Additionally, hydrolysis of the intermediate is typically not quantitative and the by-products of the process cannot be easily disposed of or recycled into the process.

DISCLOSURE OF INVENTION

It has now been found that difluoroacetic acid can be obtained from tetrafluoroethylene and unexpensive reagents without the formation of by-products requiring expensive separation and purification procedures. The reaction proceeds with high selectivity in difluoroacetic acid.

Accordingly, object of the present invention is a process for the preparation of difluoroacetic acid comprising reacting tetrafluoroethylene with an aqueous solution of an inorganic base.

Non limiting examples of suitable inorganic bases for the preparation of the aqueous base solution are alkaline and alkaline earth metal carbonates, alkaline and alkaline earth metal bicarbonates, alkaline and alkaline earth metal hydroxides, alkaline and alkaline earth metal oxides, alkaline and alkaline earth metal phosphates, alkaline and alkaline earth metal hydrogen phosphates. Preferably the inorganic base for the preparation of the aqueous base solution is selected from the group consisting of alkaline and alkaline earth metal hydroxides, namely LiOH, NaOH, KOH, CsOH, RbOH, $Ca(OH)_2$, $Ba(OH)_2$, $Mg(OH)_2$. More preferably the inorganic base is selected from the group consisting of NaOH, KOH, $Ca(OH)_2$, $Ba(OH)_2$, $Mg(OH)_2$. Even more preferably the inorganic base is selected from NaOH and KOH.

The concentration of the inorganic base in the aqueous base solution is typically in the range from 0.05 to 15 M, preferably between 0.5 and 10 M.

The process is carried out by feeding gaseous tetrafluoroethylene to the aqueous base solution.

The equivalent ratio between the inorganic base dissolved in the aqueous solution and tetrafluoroethylene is typically comprised between 1:1 and 50:1, preferably between 1.5:1 and 10:1.

The process may be carried out by feeding tetrafluoroethylene to an aqueous base solution alone. Alternatively, the process may be carried out by feeding tetrafluoroethylene to a liquid phase comprising an organic phase in addition to the aqueous base solution. The presence of an organic phase may advantageously provide an increase of the solubility of tetrafluoroethylene in the liquid system in which the reaction takes place, thus increasing the rate of conversion of tetrafluoroethylene.

Suitable organic solvents may be selected among aliphatic and aromatic compounds, halogenated aliphatic compounds, ethers, alcohols, glycols, ketones, esters, amides. Among halogenated aliphatic compounds mention can be made of hydro(fluoro)carbons, hydrofluoro(poly)ethers, chlorinated hydrocarbons, perfluorocarbons, perfluoro(poly)ethers, perfluorotrialkylamines. Among the perfluorocarbons 1,1,1,3,3-pentafluorobutane may be mentioned as a suitable organic solvent.

Typically, the organic solvent is selected among aprotic polar solvents such as diethylene glycol dimethyl ether (diglyme), dimethylformamide, diethylformamide, tetrahydrofuran, dimethylsulfoxide, dimethylacetamide, acetonitrile, 2-methoxyethyl ether, diethyl ether and their mixtures.

The amount of organic solvent in the liquid phase is not critical. Typically the ratio by volume of the organic solvent with respect to the aqueous base solution ranges from 0.1:1 up to 10:1, preferably from 0.5:1 up to 5:1.

Depending on the organic solvent the liquid phase may be mono- or biphasic.

A phase transfer catalyst, that is a catalyst that facilitates the migration of a reactant from one phase into another phase where reaction occurs, may be used in the process of the invention. Its use may be advantageous when the process is carried out in a biphasic liquid system to increase the rate of reaction. Non-limiting examples of suitable phase transfer catalysts are quaternary ammonium or phosphonium salts, e.g. ammonium or phosphonium tetrabutyl halide, ammonium or phosphonium trioctyl benzyl halide, mixtures of quaternary ammonium or phosphonium salts with other salts such as sulphonium salts can also be used.

The reaction pressure is not critical to the process. Typically, tetrafluorethylene is fed to the aqueous base solution at a pressure of from 0.1 MPa to 1.2 MPa, preferably at a pressure of from 0.1 MPa to 0.5 MPa. Tetrafluoroethylene may optionally be mixed with an inert gas. Suitable inert gases are for instance nitrogen, helium, argon, preferably nitrogen. The use of an inert gas in the process may serve as a diluent to reduce the concentration of tetrafluoroethylene below the point where it is flammable.

The reaction may be conducted at any suitable temperature, generally at a temperature in the range of from 10° C. to 180° C., preferably in the range of from 15° C. to 150° C., and more preferably in the range of from 20° C. to 120° C.

The reaction time is typically between 0.5 to 100 hours, preferably between 1 to 50 hours, and more preferably between 5 to 30 hours.

The process may be carried out in continuous, that is continuously feeding tetrafluoroethylene and extracting the liquid phase from the reaction vessel. Alternatively, the process may be carried out batch-wise, by feeding a fixed amount of tetrafluoroethylene to the liquid phase and then recovering the product from the liquid phase at the end of the reaction.

At the end of the reaction the liquid phase typically contains the reaction product in the form of a salt of difluoroacetic acid of formula $(CF_2HCOO)_n$ M, wherein M is a metallic cation of valency n. Typically M is selected from the alkaline and alkaline earth metallic cations, that is from the group consisting of Li, Na, K, Rb, Cs, Ca, Mg, Sr, Ba and n is an integer equal to 1 or 2. Preferably M is Li, Na, K when n=1 or M is Ca, Mg, Ba when n=2. More preferably M is Na or K and n=1.

The selectivity of the process to convert tetrafluoroethylene into the difluoroacetic acid salt $(CF_2HCOO)_n$M is typically greater than 90%, generally greater than 95% and even up to 99%.

The salt of formula $(CF_2HCOO)_n$M can be converted to difluoroacetic acid by any conventional hydrolysis method which is known to those skilled in the art. Typically, hydrolysis is carried out by treatment with a concentrated aqueous acid solution. The conversion of $(CF_2HCOO)_n$M to difluoroacetic acid is generally quantitative.

The inventive process has been found to be particularly advantageous as no by-products are formed in any of the process steps, even when the yield in the difluoroacetic acid salt is low. In particular no by-products which require separation and appropriate disposal are formed by the inventive process.

When the reaction of tetrafluoroethylene with the inorganic base solution is carried out in the presence of an organic phase it may be preferable, before hydrolysis to remove the organic phase. The organic phase may be separated from the aqueous phase by any conventional method, for instance by evaporation under vacuum.

Difluoroacetic acid can then be recovered from the aqueous phase with standard isolation and purification techniques.

The invention will be now described in more detail with reference to the following examples, whose purpose is merely illustrative and not intended to limit the scope of the invention. Should the disclosure of any patents, patent applications, and publications which are incorporated herein by reference conflict with the description of the present application to the extent that it may render a term unclear, the present description shall take precedence.

EXAMPLES

Example 1

An aqueous solution of KOH 10 M (78 ml) and dimethylformamide (50 ml) were charged in a 250 ml AISI 316 autoclave. The autoclave was cooled to −50/−70° C. and evacuated under reduced pressure. The temperature was raised to 75° C. under magnetic stirring. Tetrafluoroethylene (a total of 0.25 moles) was continuously fed to the liquid phase at a pressure of 0.3 MPa. The liquid mixture was stirred for 20 hours. After cooling to room temperature, the liquid mixture was discharged and analyzed by NMR spectroscopy: conversion of tetrafluoroethylene to $CF_2HCOOK$ was quantitative with complete reaction of tetrafluoroethylene.

The crude mixture was heated to 100° C. under reduced pressure to remove the solvents. The remaining liquid mixture was acidified by addition of concentrated HCl while cooling and then extracted several times with diethyl ether (diethyl ether/HCl: 1/1 v/v). The organic extract was dried over $MgSO_4$ before fractional distillation of the dried ether extract. 23 g (0.24 moles) of difluoroacetic acid having 98% purity were isolated.

Example 2

Using the same procedure as Example 1 tetrafluoroethylene (0.14 moles) was reacted with a 7.5 M solution of NaOH (60 ml) in the presence of diglyme (60 ml). A biphasic liquid mixture was formed. After 24 hours the reaction was complete and the biphasic crude mixture was discharged in a separatory funnel. After separation the two phases were analyzed: both of them contained $CF_2HCOONa$ as the only product. The selectivity of the reaction of tetrafluoroethylene to $CF_2HCOONa$ was quantitative. The upper organic phase was extracted twice with a 2% solution of NaOH and the resulting aqueous phase separated.

The collected aqueous phases, were brought together, acidified by addition of 20% solution of HCl and then extracted several times with diethyl ether and isolated as described in example 1. 12.9 g (0.14 moles) of difluoroacetic acid having 98% purity were isolated.

Example 3

Using the same procedure as Example 1 tetrafluoroethylene (0.1 moles) was reacted with a 10 M solution of KOH (78 ml) in the presence of acetonitrile (60 ml). After 22 hours the liquid mixture was discharged and analyzed by NMR spectroscopy: conversion of tetrafluoroethylene to $HCF_2$ COOK was quantitative with complete reaction of tetrafluoroethylene.

The isolation of the product was carried out as in Example 1 giving 9.2 g (0.1 moles) of difluoroacetic acid with 98% purity.

Example 4

Using the same procedure as Example 1, an aqueous solution of NaOH 7.5 M (60 ml) was charged together with 40 ml of a perfluoropolyether solvent, GALDEN® PFPE, having an average boiling point of 130° C., and 3 ml of a 40% solution of tetrabutyl ammonium hydroxide in a 250 ml AISI 316 autoclave. The autoclave was connected to a 1 liter reservoir of tetrafluoroethylene at 0.3 MPa and heated to 75° C. for 20 hours. The liquid mixture was then discharged and analyzed by NMR spectroscopy: the amount of tetrafluoroethylene that reacted to yield $CF_2HCOONa$ was low but without formation of by-products. The selectivity based on converted tetrafluoroethylene was quantitative. Yield in $CF_2HCOONa$ was 12%.

Example 5

Using the same procedure as Example 1, an aqueous solution of NaOH 7.5 M (60 ml) was charged in a 250 ml AISI 316 autoclave, the autoclave was pressurized with 0.3 MPa of tetrafluoroethylene and heated to 75° C. for 20 hours under stirring. The liquid mixture was then discharged and analyzed by NMR spectroscopy. Although the yield in $CF_2HCOONa$ was low (1.0% with respect to tetrafluoroethylene) no by-products were formed as all the reacted tetrafluoroethylene was converted into $CF_2HCOONa$.

Example 6

Using the same procedure of Example 1, an aqueous solution of $K_2CO_3$ 1.5 M (7 ml) and diglyme (15 ml) were charged in a 100 ml AISI 316 autoclave. A biphasic liquid mixture was formed. The autoclave was pressurized with 0.3 MPa of tetrafluoroethylene and heated at 75° C. under magnetic stirring. After 54 hours the reaction was stopped and the biphasic crude mixture was discharged in a separatory funnel. After separation, the two phases were analyzed by NMR. Although the yield in $CF_2HCOONa$ was low (4.1% with respect to tetrafluoroethylene) no by-products were formed as all the reacted tetrafluoroethylene was converted into $CF_2HCOONa$.

The invention claimed is:

1. A process for the preparation of difluoroacetic acid comprising the step of reacting tetrafluoroethylene with an aqueous solution of an inorganic base to obtain a difluoroacetic acid salt wherein the inorganic base is selected from the group consisting of alkali and alkaline earth metal carbonates, alkali and alkaline earth metal bicarbonates, alkali and alkaline earth metal hydroxides, alkali and alkaline earth metal oxides, alkali and alkaline earth metal phosphates, and, alkali and alkaline earth metal hydrogen phosphates.

2. The process according to claim 1 wherein the inorganic base is selected from the group consisting of LiOH, NaOH, KOH, CsOH, RbOH, $Ca(OH)_2$, $Mg(OH)_2$, $Sr(OH)_2$, and $Ba(OH)_2$.

3. The process according to claim 1 wherein the concentration of the inorganic base in the aqueous solution ranges from 0.05 to 15 M.

4. The process according to claim 1 wherein the equivalent ratio between the inorganic base in the aqueous solution and the tetrafluoroethylene is between 1:1 and 50:1.

5. The process according to claim 1 carried out in the presence of at least one organic solvent.

6. The process according to claim 5 wherein the ratio by volume of the at least one organic solvent to the aqueous base solution is from 0.1:1 to 10:1.

7. The process according to claim 5 wherein the organic solvent is selected from the group consisting of aliphatic and aromatic compounds, halogenated aliphatic compounds, ethers, alcohols, glycols, ketones, esters, and amides.

8. The process according to claim 5 wherein the organic solvent is a polar aprotic solvent.

9. The process according to claim 8 wherein the organic solvent is selected from the group consisting of diethylene glycol dimethyl ether, dimethylformamide, diethylformamide, tetrahydrofuran, dimethylsulfoxide, dimethylacetamide, acetonitrile, 2-methoxyethyl ether, diethyl ether and their mixtures.

10. The process according to claim 5 carried out in the presence of a phase transfer catalyst.

11. The process according to claim 1 further comprising a step of hydrolyzing said difluoroacetic acid salt to obtain difluoroacetic acid.

* * * * *